United States Patent [19]

Josephson et al.

[11] Patent Number: 5,336,506
[45] Date of Patent: Aug. 9, 1994

[54] TARGETING OF THERAPEUTIC AGENTS USING POLYSACCHARIDES

[75] Inventors: Lee Josephson, Arlington; Ernest V. Groman, Brookline; Chu Jung, Arlington; Jerome M. Lewis, Newton, all of Mass.

[73] Assignee: Advanced Magnetics Inc., Cambridge, Mass.

[21] Appl. No.: 936,873

[22] Filed: Aug. 27, 1992

Related U.S. Application Data

[63] Continuation of Ser. No. 630,017, Dec. 19, 1990, abandoned, which is a continuation-in-part of Ser. No. 679,526, Apr. 2, 1991, Pat. No. 5,141,739, and a continuation-in-part of Ser. No. 384,991, Jul. 2, 1989, abandoned, which is a continuation-in-part of Ser. No. 228,640, Aug. 4, 1988, abandoned, which is a continuation-in-part of Ser. No. 67,586, Jun. 26, 1987, Pat. No. 4,827,945, which is a continuation-in-part of Ser. No. 882,044, Jul. 3, 1986, Pat. No. 4,770,183.

[51] Int. Cl.$^5$ .......................... A01K 31/715
[52] U.S. Cl. ................... 424/488; 424/646; 435/178; 514/2; 514/21; 514/54; 514/169; 514/179; 536/55.1
[58] Field of Search .......... 424/493, 646, 488; 435/178; 514/54, 2, 21, 169, 179; 530/813; 536/55.1

[56] References Cited

U.S. PATENT DOCUMENTS

| | | | |
|---|---|---|---|
| 4,501,726 | 2/1985 | Schroder et al. | 424/1.1 |
| 4,770,183 | 9/1988 | Groman et al. | 128/654 |
| 4,827,945 | 5/1989 | Groman et al. | 128/653 |
| 4,861,597 | 8/1989 | Kida et al. | 424/450 |
| 4,946,675 | 8/1990 | Baldwin et al. | 514/2 |

FOREIGN PATENT DOCUMENTS

| | | |
|---|---|---|
| 0186947 | 7/1986 | European Pat. Off. |
| 0281809 | 9/1988 | European Pat. Off. |
| 3738069 | 5/1989 | Fed. Rep. of Germany |
| 9001295 | 2/1990 | PCT Int'l Appl. |
| 9003190 | 4/1990 | PCT Int'l Appl. |

OTHER PUBLICATIONS

Wu et al., JBC, 263, p. 14621, (1988).
Fallon et al., Hepatology, 5, p. 899, 1985.
Meizer et al., Pharmaceutical Res., 6, 105, (1989).
Dasgupta et al., (1985), Biochemistry International, 10, pp. 327–338.
Ghosh et al., (1982), Proc. Indian. Natn. Sci. Acad., 48, pp. 12–19.
Ponpipom et al., (1983), Carbohydrate Research, 118, pp. 47–55.
International Search Report for International Application PCT/US91/09368 derived from U.S. patent application 07/630,017 described above.
Bodmer and Dean, (1985), Method in Enzymology, 112, pp. 298–306.
Brown et al., (1978), Arch. Bioch. Biophys., 188, pp. 418–428.
Dragsten et al., (1987), Biochim. Biophys. Acta, 926, pp. 270–279.
Fallon and Schwartz, (1985), Hepatology, 5, pp. 899–901.

(List continued on next page.)

*Primary Examiner*—G. S. Kishore
*Attorney, Agent, or Firm*—Bromberg & Sunstein

[57] ABSTRACT

The invention relates to a method for the targeting of a therapeutic agent to a specific population of cells, wherein a complex is formed between the therapeutic agent and a polysaccharide capable of interacting with a cell receptor, and wherein the resulting complex is internalized into the cell by receptor mediated endocytosis (RME). In one embodiment of the invention, a complex of a therapeutic agent containing iron and the polysaccharide arabinogalactan may be formed and used to deliver iron specifically to hepatocytes by RME.

13 Claims, 1 Drawing Sheet

OTHER PUBLICATIONS

Glicksman, ed., (1982), "Food Hydrocolloids", CRC Press, pp. 5 and 33.
Gorin and Barreto-Bergter in "The Polysaccharides", vol. 2, G. O. Aspinall, ed., Academic Press, 1983, pp. 376-380.
Harford and Ashwell in "The Glycoconjugates", vol. IV, M. I. Horowitz, ed., Academic Press, 1982, pp. 27-55.
Hamstra et al., (1980), JAMA, 243, pp. 1726-1731.
Henderson and Hillman, (1969), Blood, 34, pp. 357-375.
Martin, C. R., (1976), "Textbook of Endocrine Physiology", Williams & Wilkins, p. 21.
Meijer and van der Sluijs, (1989), Pharm. Res., 6, pp. 105-118.
Mukhopadhyay et al., (1989), Science, 244, pp. 705-707.
Ranade, V. V., (1989), J. Clin. Pharmacol., 29, pp. 685-694.
Stockert and Becker, (1980), Cancer Res., 40, pp. 3632-3634.
Wileman et al., (1985), Biochem. J., 232, pp. 1-14.
Wu and Wu, (1988), J. Biol. Chem., 263, pp. 14621-14624.
Lee et al., (1984), Biochemistry, 23, pp. 4255-4261.
Josephen et al., (1990), Magnetic Resonance Imaging, 8, pp. 637-646.

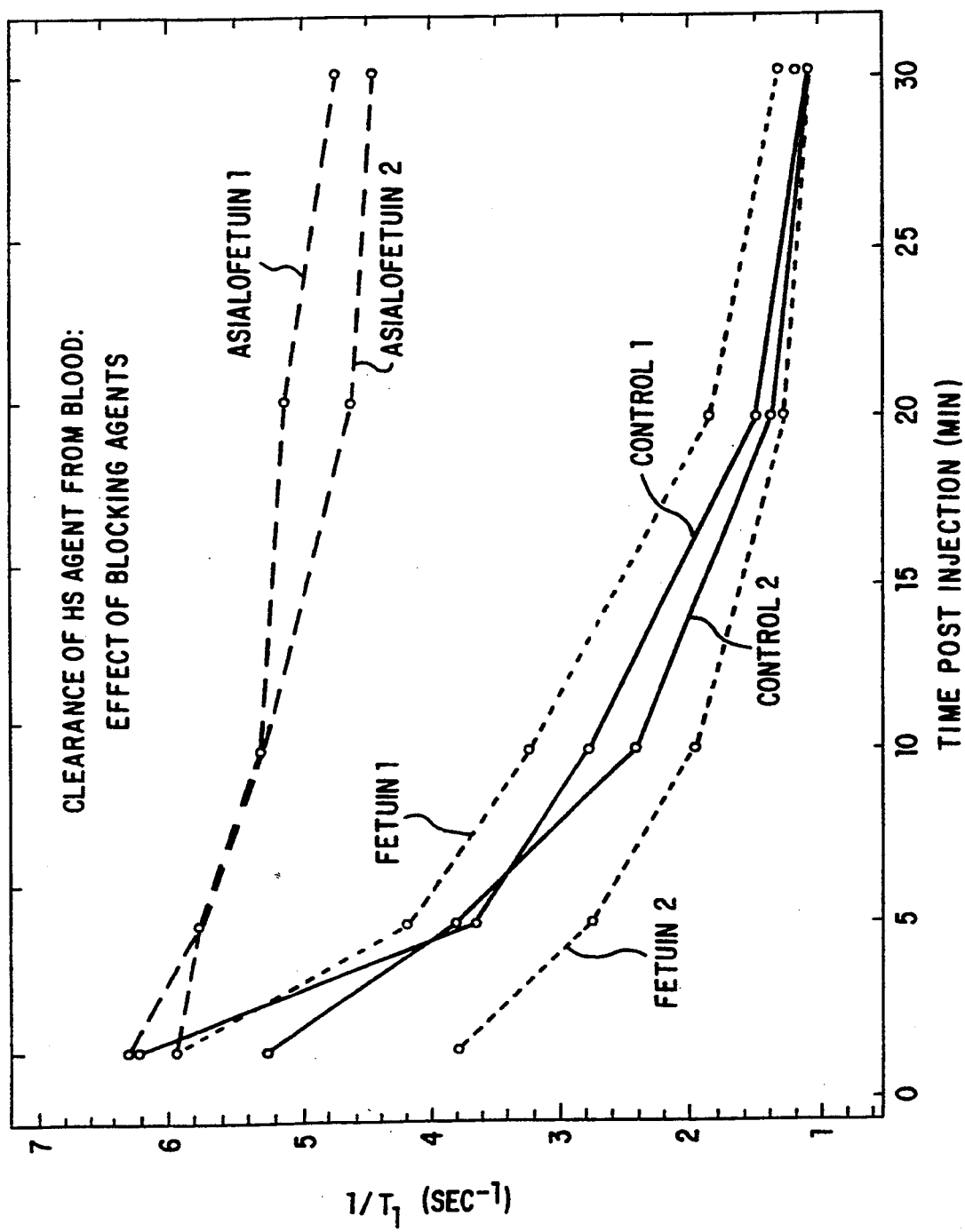

TARGETING OF THERAPEUTIC AGENTS USING POLYSACCHARIDES

CROSS REFERENCE TO RELATED APPLICATIONS

This is a continuation of copending application(s) Ser. No. 07/630,017, filed on Dec. 19, 1990, now abandoned which is a continuation-in-part of U.S. application Ser. No. 07/679,526 filed Apr. 2, 1991, now U.S. Pat. No. 5,141,739, and a continuation-in-part of U.S. application Ser. No. 07/384,991 filed Jul. 28, 1989, now abandoned which is a continuation-in-part of U.S. application Ser. No. 07/228,640 filed Aug. 4, 1988, now abandoned, which is a continuation-in-part of U.S. application Ser. No. 067,586 filed Jun. 26, 1987, now U.S. Pat. No. 4,827,945, which in turn a continuation-in-part of U.S. application Ser. No. 882,044, filed Jul. 3, 1986, now U.S. Pat. No. 4,770,183. These related applications are hereby incorporated herein by reference.

TECHNICAL FIELD

The present invention relates to methods for the targeting of a therapeutic agent to a specific population of cells, especially hepatocytes.

BACKGROUND ART

Before reviewing the background art, it is useful to define certain terms. A therapeutic agent is one administered with the intent of changing in a beneficial manner some physiological function of the recipient. Therapeutic agents include drugs, proteins, hormones, enzymes, nucleic acids, peptides, steroids, growth factors, modulators of enzyme activity, modulators of receptor activity and vitamins. A diagnostic agent is one administered with the intent of illuminating some physiological function, while leaving physiological function unaffected. Diagnostic agents include radioactive isotopes for scintigraphy, electron dense labels for X-ray or computer tomography, and magnetic labels for magnetic resonance imaging.

Targeting is the modification of an agent so that after parenteral administration its uptake by a specific type or population of cells is increased, over that obtained with the unmodified agent.

Receptor mediated endocytosis (RME) is a process whereby molecules in the extracellular space bind to specific receptors on the cell surface and are internalized. Through the process known as RME, molecules injected into the vascular compartment are cleared (removed) from plasma.

Uptake by RME exhibits three general properties characteristic of ligand-receptor interactions generally: structural specificity, saturability and competition. Structural specificity is observed when a receptor can distinguish between closely related structures and only molecules with structures meeting the binding requirements of the receptor binding site are internalized. Often the receptors involved in RME are discovered by their ability to internalize or clear glycoproteins from circulation. Saturability is observed when the rate of an agent internalized via RME decreases with increasing concentrations of that agent. This results because, at high concentrations, the receptor approaches full occupancy or becomes saturated with ligand.

Competition is observed when the rate of internalization of an agent can be reduced by the presence of additional agents bearing a structural resemblance to the first agent. The additional agents compete for receptor binding sites and decrease the rate of internalization of the first agent. Saturability results when high concentrations of a single ligand compete for a limited number of receptor sites. Competition results when chemically different ligands bind to a limited number of receptor sites.

The uptake of substances by RME is a feature of normal, healthy cells. RME transport systems can be found on normal macrophages, hepatocytes, fibroblasts, and reticulocytes. RME enables cells to internalize a variety of macromolecules in plasma, such as asialoglycoproteins, low density lipoproteins, transferrin, and insulin. See Table 1 of Wileman et al. Blochem. J. 232:1–14; 1985 for a list of cells performing RME, which also contains a general review of RME. See also Table I of Menz, E. T. PCT WO 90/01295, filed Aug. 3, 1989. Conversion of normal cells to tumor cells (transformation), may be associated with an increase or decrease in the activity of receptors performing RME. In some cases, such as the RME performed by the asialoglycoprotein receptor of hepatocytes, transformation to cancerous hepatoma cells is associated with receptor loss. Stockeft and Becker, Cancer Res. 40:3632–3634; 1980. In many cases, like the antibody based targeting of drugs to tumor antigens, the antigens are increased on tumor cells and decreased on normal cells.

Polysaccharides like arabinogalactan, which interact with receptors involved in RME, are referred to as RME-type polysaccharides. Many common polysaccharides such as dextrans, dextrins, celluloses, hydroxyethylstarchs, heparins, starchs, dextran sulfates, carboxylmethylated dextran, and carboxymethyl cellulose do not interact with receptors involve in RME; they are referred to as non-RME polysaccharides.

With these definitions in hand, the relevant background art will be discussed. Non-RME type polysaccharides have been used in the synthesis of a variety of materials used as diagnostic or therapeutic agents. Jacobsen, T. EPO 0 186 947 B1; Schroder U.S. Pat. No. 4,501,726; Ranney, D. F. PCT WO 90/03190, filed Sep. 29, 1989; Groman U.S. Pat. No. 4,827,945; Groman U.S. Pat. No. 4,770,183. Ranney discloses the delivery of diagnostic agents (metal ions as magnetic resonance (MR) contrast agents), using a polymeric carrier which is directed to tumor cells. Ranney suggests, without detailed examples, that other therapeutic complexes may also be delivered using this method, for chemotherapeutic impact or to provide sensitization or augmentation for radiation treatment (Ranney, D. F. PCT WO 90/03190, filed Sep. 29, 1989, page 51). It is known that the RME-type polysaccharide arabinogalactan can be used to target certain diagnostic agents, particularly superparamagnetic iron oxide. Menz, E. T. PCT WO 90/01295, filed Aug. 3, 1988.

Therapeutic agents, on the other hand, have been typically targeted by liposomes and by glycoproteins. Normally after injection, liposomes are recognized as particulate matter and are subject to phagocytosis, which results in their concentration in the tissues of the reticuloendothelial system (RES). Materials within liposomes are then concentrated in tissues such as the liver, spleen and bone which comprise the RES. Surface-modified liposomes have been synthesized and can be cleared by RME, but the surface modification consisted of a coating of proteins or glycoproteins. Ranads, V. V., J. Clin. Pharmacol. 29:685-694; 1989; Dragsten et al. Biochim. Biophys. Acta 926:270-279; 1987.

Colloids and particles of differing sizes and compositions are recognized by the RES. For example, Imferon, a dextran coated colloidal ferric oxyhydroxide used for the treatment of anemia, is slowly cleared from the blood by the phagocytic activity of the macrophages of the RES. Henderson and Hillman, Blood 34:357-375; 1969. Radioactive diagnostic agents such the technicium sulfur colloids and many types of magnetic particles used as MR contrast agents are also cleared by the RES. For a discussion see Josephson, etal. Mag. Res. Imag. 8:637-646; 1990.

Glycoproteins internalized by RME have been used to target therapeutic agents. For a review of targeting strategies see Table II of Meijer and van der Sluijs, Pharm. Res. 6:105-118; 1989.

SUMMARY OF THE INVENTION

The present invention provides a method of targeting a therapeutic agent to a specific population of cells. Targeting may be accomplished by forming a complex between a therapeutic agent and a polysaccharide capable of interacting with receptors performing receptor mediated endocytosis (RME). The resulting complex may then be internalized into the specific population of cells by receptor mediated endocytosis. The invention enables the concentration of therapeutic agents to be increased in tissues where they have beneficial actions and decreased in tissues where they have unwanted, toxic effects. In one embodiment of the invention, the therapeutic agent may include a composition containing iron, and the polysaccharide may be arabinogalactan. In this embodiment, a complex of arabinogalactan and a composition containing iron may be formed and used to deliver iron specifically to hepatocytes by RME.

BRIEF DESCRIPTION OF THE DRAWINGS

The foregoing features of the invention will be more readily understood by reference to the following detailed description taken with the accompanying drawings, in which:

FIG. 1 is a graph illustrating the effect of asialofetuin or fetuin on the clearance of an RME-polysaccharide-therapeutic agent complex (in accordance with an embodiment of the invention), to illustrate the specificity of the targeting of this delivery system.

DETAILED DESCRIPTION OF SPECIFIC EMBODIMENTS

GENERAL

The invention provides a method of targeting a therapeutic agent into a specific population of cells. Targeting increases the concentration of the therapeutic agent in cells where the agent exerts some beneficial action, and reduces its concentration in other cells where unwanted, toxic effects are being produced. Many therapeutic agents produce toxic effects, not upon the cells where the agent has a beneficial action, but on cells other than those responsible for the beneficial action.

By targeting therapeutic agents towards certain cells, and away from other cells, the invention provides a way of improving the safety and efficacy of previously developed therapeutic agents. For example, a therapeutic agent intended to modify the metabolism of the hepatocytes of the liver, might exhibit toxic effects to bone marrow cells. Since bone marrow function is essential for life, toxic effects on marrow limit the dose of the agent that can be given. If the agent were targeted to hepatocytes by attachment to the arabinogalactan, the concentration to bone marrow would be reduced. The potency of the agent would be improved, because the fraction of the therapeutic agent which normally goes to bone marrow is now directed to the liver. Bone marrow related side effects would be eliminated.

Distinguishing the RME-type Polysaccharides Used by the Invention

With the current invention, a therapeutic agent is attached to an RME-type polysaccharide and the resulting complex is targeted into specific types of cells through the action of cell surface receptors. Only certain polysaccharides may be used in the invention and these are termed RME-type polysaccharides. RME-type polysaccharides differ from common, non-RME polysaccharides, e.g. dextrans, dextrins, celluloses, hydroxyethylstarchs, heparins, starchs, dextran sulfates, carboxylmethylated dextran, and carboxymethyl cellulose. Non-RME polysaccharides are used in diverse applications such as drug delivery, drug formulation, as food additives and in plasma volume expansion. RME-type polysaccharides include arabinogalactan mannan and fucoidan, and may be used, according to the invention, to deliver therapeutic agents directly to hepatocytes and macrophages respectively. References, such as Ranney, described above, concerning the delivery of certain therapeutic agents using polysaccharides, do not disclose or concern themselves with the use of RME-type polysaccharides.

Below, we refer to the complex of the invention as the RME-type polysaccharide-therapeutic agent complex. The complex between the RME-type polysaccharide and the therapeutic agent can involve the covalent attachment of the therapeutic agent to the PME-type polysaccharide (Examples 2 and 3), a colloid coated with polysaccharide (Example 1), or a liposome coated with an RME-type polysaccharide.

Chemical modifications of non-RME polysaccharides have been achieved, including carboxymethylation, succinylation, hydroxyethylation, and sulfation. Generally, such chemical modification of common polysaccharides does not confer the ability to bind to a receptor and undergo RME.

However, non-RME polysaccharides can, in some instances, be modified by the attachment of substituent groups that are recognized by receptors performing RME, and such modifications confer the property of RME on non-RME polysaccharides. For example, a galactose residue can be attached to the non-RME polysaccharide dextran; the galacross of the resulting polysaccharide will be recognized by the asialoglycoprotein receptor and undergo RME. By attachment of galactose, the dextran is converted into an RME-type polysaccharide. Similarly, a mannose group can be attached to dextran and the resulting polysaccharide will be recognized by the mannose receptor of phagocytes.

A second modification of RME type polysaccharides involves partial digestion to produce lower molecular weight polysaccharides. This can be accomplished by controlled hydrolysis with acid and fractionation to obtain RME-type polysaccharides in the desired size class. The polysaccharides of the invention, before degradation or modification, have molecular weights greater than about 1,000 daltons.

For a polysaccharide to be designated an RME-type polysaccharide, its binding to a receptor performing RME must be demonstrated. One type of demonstration involves the ability of an RME-type polysaccharide to block the clearance of a glycoprotein known to be cleared by RME. For example, the interaction of arabinogalactan with the asialoglycoprotein receptor was demonstrated by its ability to block the clearance of a radioactive sample of the asialoglycoprotein, asialofetuin. Injection of 500 mg/kg of arabinogalactan blocks the clearance of $^{125}$I-asialofetuin in rats. (See Table 1 of Josephson, et al., Mag. Res. Imag. 8:637–646; 1990.) AS a result of this experiment as well as others, it can be concluded that arabinogalactan is recognized by the asialoglycoprotein receptor of hepatocytes. Consequently arabinogalactan is an RME-type polysaccharide.

Similarly mannan blocks the clearance of radioactive glycoprotein, RNase B. Brown, etal. Arch. Bioch. Biophys. 188:418–428; 1978. Arabinogalactan and mannan are discussed briefly below. In addition to the polysaccharides discussed explicitly herein, other RME-type polysaccharides may be formed as modification or degradation products of the polysaccharides discussed.

A simple test for whether a polysaccharide-therapeutic agent complex is of the type covered by the invention is afforded by ability of various substances to slow the elimination of the complex from blood (clearance). The complexes of the invention are cleared by RME, and their clearance is blocked by substances cleared by the same receptor. As shown in FIG. 1, asialofetuin, which is cleared by an RME receptor on hepatocytes, blocks the clearance of the arabinogalactan iron oxide colloid of Example 1. Asialofetuin will not block the clearance of many other colloids or particles coated with surfaces that do not interact with the receptors performing RME.

The clearance of the RME-type polysaccharide-therapeutic agent complexes of the invention is unaffected by the injections of substantial concentrations of non-RME type polysaccharides, e.g. dextran and hydroxyethyl starch. The clearance of the RME-polysaccharide-therapeutic agents of the invention is also unaffected by the injection of substantial concentrations of particles, colloids or liposomes cleared by the phagocytic cells of the RES.

Advantages of Polysaccharides as Carriers for the Delivery of Therapeutic Agents An advantage of using polysaccharides instead of proteins for the delivery of therapeutic agents is that polysaccharides do not denature readily at high temperature, extremes of pH or in organic solvents. In Example 1, the polysaccharide arabinogalactan is used as a coating for an iron oxide colloid. During that synthesis, arabinogalactan is exposed first to a pH below about 3, when soluble iron salts are present, then to a high pH after base addition and finally to a high temperature. Because of the stability of polysaccharides, covalent linkages between therapeutic agents and polysaccharides can be achieved in organic solvents. This is a considerable advantage since some therapeutic agents have low water solubility. A related advantage of polysaccharides of working in nonaqueous media is that water unstable linkages like esters can be created between the therapeutic agent and the polysaccharide. An example of such chemistry is provided by Example 3.

Another advantage of polysaccharides is that they can be obtained from microbiological or plant sources. Glycoproteins from human or animal sources may contain pathogens whose absence is costly to assure. Polysaccharides from microbiological or plant sources can be selected for use in the invention which are of very low toxicity and immunogenicity. Plant or microbiological sources can provide crude polysaccharide preparations on a large scale, in a reliable manner and at a reasonable price. Two classes of carbohydrates which can be utilized in the invention are the arabinogalactans and the mannans.

Arabinogalactans

Arabinogalactans are a class of polysaccharides that may be obtained from the cell walls of many species of trees and plants. A common source of arabinogalactan is the American western latch (Larix occidentalis). Arabinogalactan from this source is used as a binder, emulsifier or stabilizer in foods. It consists of a galactose backbone with branch chains of arabinoses and galactose. Generally the ratio of galactose to arabinose is between 5 to 1 and 10 to 1. The molecular weight can be between 10 to 100 kilodaltons. "Food Hydrocolloids," Glicksman, ed., CRC Press, 1982, p.5 and p.33.

Best results are obtained when a purified arabinogalactan is used. Commercially available arabinogalactan can be further purified by ultrafiltration to remove impurities greater than 100,000 daltons and smaller than 10,000 daltons. Arabinogalactan purified by this method is used in the examples of the patent. The arabinogalactan used in Examples 1–3 was subjected to purification in this manner.

Arabinogalactans bind to the asialoglycoprotein receptor of hepatocytes. This receptor performs RME on a variety of substances. Harford and Ashwell in "The Glycoconjugates," vol. IV, M. I. Horowitz, Ed., Academic Press, 1982 pp. 27–55. Therapeutic agents attached to arabinogalactan will be targeted to hepatocytes.

Mannans

Mannans are a class of polysaccharides that can be obtained from the cells walls of yeasts. They are predominately α-D-mannopyrans with a variety of linear and branched chain structures. P. A. J. Gorin and E. Barreto-Berger in "The Polysaccharides," G. O. Aspinall, vol. 2 Academic Press, 1983, pp. 376–380.

Mannans bind to the mannose receptor found on the macrophages of the RES. Therapeutic agents attached to mannan will be targeted to macrophages.

Therapeutic Agents Targeted by the Invention

Utilizing the methods of the invention, a wide variety of therapeutic agents may be targeted to a population of cells. Examples of such therapeutic agents are listed in Table 1. Some of the agents in Table i may be targeted to hepatocytes, such as antiviral agents for the treatment of hepatitis. Iron may be targeted to hepatocytes to remedy nutritional imbalance, i.e. iron deficiency anemia. When genetic defects are expressed in the liver, such as the deficiency of a hepatic enzyme, DNA may be targeted to the liver to alter the genetic defects. The invention may be used to target therapeutic agents that have been targeted by other techniques. Other summaries of therapeutic agents whose targeting has been attempted are available. See Table II of Meijer and van der Sluijs, Pharm. Res. 6:105–118; 1989 and Ranade, J. Clin. Pharmacol. 29:685–694; 1989.

TABLE 1

Applications and Agents Targeted By the Invention

| Agent | Application | Reference |
|---|---|---|
| Iron | treatment of anemia | Example 1 |
| Ara A-phosphate | hepatitis treatment | Bodmer & Dean Methods in Enzymology 112:298–306; 1985. |
| Trifluorthymidine | hepatitis treatment | above |
| DNA | genetic defect reversal | Wu and Wu, J. Biol. Chem. 263:14621–14624; 1988. |
| Methotrexate | treatment of leishmaniasis | Mukhopadhyay et al. Sci. 244:705–707; 1989. |

The targeting of antiviral agents into hepatocytes of an individual, chronically infected with hepatitis B virus, is an application of the invention where anti-vital agents would be the therapeutic agents targeted. The targeting of an antiviral agent to the infected cell population (hepatocytes), and away from bone marrow, may result in more effective treatment with the drug. Antiviral agents may be attached to arabinogalactan, and injected intravenously, to achieve a high concentration in the hepatocytes. The targeting of nutritionally required substances such as iron may be targeted by the invention. In Example 1, an arabinogalactan colloid is synthesized which targets iron by RME in accordance with the teachings of the current invention. Parenterally administered iron has often been used in the treatment of anemia, in the form of an iron oxide dextran complex called Imferon. The iron oxide dextran is slowly removed from blood by the RES. Imferon exhibits some tendency to produce adverse reactions. Hamstra, et al. JAMA 243:1726–1731; 1980. In contrast, iron oxides made with arabinogalactan (see Example 1) are rapidly cleared by RME and targeted to the hepatocytes of the liver. This difference in pharmacokinetics and biodistribution may result in the iron of the invention being a safer therapeutic agent than iron oxide dextran.

Vitamins may also be targeted by the invention. Example 2 shows the preparation of a folic acid arabinogalactan conjugate, which would target the vitamin folic acid to hepatocytes via RME. Folic acid is chemically similar to the drug methotrexate, which can be coupled to arabinogalactan by minor modifications of the procedure shown for folic acid.

Hormones such as steroids may be delivered directly to a specific population of cells utilizing the methods of the invention. Steroids have powerful biological activities which are exerted after the steroid binds to a receptor present on the cells. Martin, C. R. "Textbook of Endocrine Physiology," (1976) Williams & Wilkins, p. 21. The targeting of steroids to cells is a widely useful application of the invention. One application of targeting hormones involves targeting glucocorticoid steroids into cells. Example 3 presents a synthesis of an arabinogalactan-prednisone conjugate which may serve to target the steroid prednisone via RME into hepatocytes. Steroids could be targeted by attachment to mannan, and targeted into appropriate cells by the mannose receptor present on cells of the RES.

EXAMPLES

Example 1

An colloidal iron oxide coated with arabinogalactan was prepared for the treatment of iron deficiency. An arabinogalactan coated superparamagnetic (or paramagnetic) iron oxide as in Example 6.10.1 of WO 90/01295 was prepared. An aqueous solution of $FeCl_3$ (15.8 g, 58.5 mole and $FeCl_2 \cdot 4 H_2O$ (6.24, 31.6 mmoles) is prepared and filtered through a 0.22 micron filter to remove large debris. Equal volumes of iron salts and a solution of arabinogalactan from latch wood (60 g, Sigma Chemical Co.) in distilled water (120 mL) are combined at ambient temperature with vigorous stirring. A 30% aqueous ammonium hydroxide solution is then added to the mixture, slowly and dropwise, until the pH reaches about 10. The mixture is then heated to a temperature of about 90°–100° C. for about 15 minutes. The mixture is allowed to cool and filtered through filters of decreasing porosity of 0.8, 0.45 and 0.22 microns.

Excess arabinogalactan is then removed by ultrafiltration step using a 2 liter hollow fiber unit having a 300 kilodalton cutoff (Amicon, Inc., Danvers, Mass.). The filtered product from the preceding step is loaded into the ultrafiltration unit and washed by the addition of a buffer of 25 mM sodium citrate (pH 8.5). The washing is repeated about five times or until a clear eluent is observed. The washed product is then concentrated back to the initial volume of polysaccharide plus metal solutions.

Because the polysaccharide arabinogalactan has been used as a coating for the iron colloid, it is cleared by the asialoglycoprotein receptor of hepatocytes. The presence of injected iron in the liver, and not in the spleen, indicates the targeting of iron into a specific cell population (hepatocytes) has been achieved. For data see Table 2 of Josephson, et al., Mag. Res. Imag 8:637–646:1990, or Table V of Menz et al. PCTWO 90/01295.

The therapeutic potential of the arabinogalactan coated iron oxide is shown when $^{59}Fe$ is used in the synthesis. The iron is incorporated over a period of days into normal body iron pools, such as the iron found in hemoglobin. Hence, an arabinogalactan form of iron oxide could be a therapeutic agent when used in the treatment of iron deficiency anemia.

Example 2

Folic acid is a vitamin which has been coupled to a polysaccharide undergoing RME called arabinogalactan as described below. The drug methotrexate is a folic acid antagonist and anticancer drug. Methotrexate may be attached to polysaccharides undergoing RME and used in drug delivery applications, by modifying the folic acid coupling chemistry shown below.

Folic acid dihydrate (6.0 mg, 13 μmol) was suspended in $H_2O$ (1 mL). NaOH (0.10N, 7 drops) was added until the white solid folic acid was almost completely dissolved. Purified arabinogalactan (23,000 daltons; 35.3 mg, 1.53 μmol) was added, followed by 1-(3-dimethylaminopropyl)-3- ethylcarbodiimide (51.2 mg, 286 μmol). After stirring for 2.5 hours at room temperature, the reaction mixture was analyzed by HPLC on a Sephadex G-25 column (9.5×300 mm) using an eluent of 0.05% $NaN_3$ (0.33 mL/min). Detection of free and coupled folic acid was accomplished by using a uV detector, set at 280 nm (for folio acid, UV-$_{max}$=283 nm, log=4.40.). The chromatogram showed a peak with a retention time of 16.8 minutes due to folate conjugated to arabinogalactan. Free folic acid appeared at 35 minutes. These assignments were obtained from chromatographing arabinogalactan and folic acid. Purified arabinogalactan required a refractive index detector as it does not absorb at 280 nm. Based on UV detection, 37% of the folic acid was coupled to arabinogalactan. Based on no loss of arabinogalactan and 37% of the folate conjugated, a folate/arabinogalactan ratio of 3:1 was obtained.

Example 3

Steroids are a class of drugs which can be delivered to cells by attaching them to polysaccharides that undergo RME. A variety of steroids may be coupled to such polysaccharides following analogous chemistry to that given below. The general steps are (i) preparation of a polysaccharide conjugate providing carboxyl groups by reaction with DTPA, (ii) attachment of the steroid through the carboxyl group of the DTPA-polysaccharide.

Preparation of arabinogalactan-DTPA

Purified arabinogalactan (23,000 daltons, 0.50 g, 21.7 μmol) and diethylenetriaminepentaacetic acid (DTPA) dianhydride (0.102 g, 285 μmol) were dissolved in DMSO (20 mL) at 60° C. After one hour, the clear solution was cooled to room temperature. Upon addition of H$_2$O (10 mL), a white precipitate formed. The mixture was filtered on an Amicon YM 5 ultrafiltration membrane (5,000 dalton cutoff), and washed with H$_2$O (4×30 mL) The product remaining on the membrane was dissolved in H$_2$O (10 mL), frozen and lyophilized. Yield of white powder: 0.44 g. The nominal DTPA/arabinogalactan ratio was 13.1, assuming attachment of all DTPA added (nominal formula weight: 28,000 daltons).

Coupling 6α-methylprednisolone to arabinogalactan-DTPA

Arabinogalactan-DTPA (107.5 mg, 3.8 μmole) and 6α-methylprednisolone (64.5 mg, 172 μmol) were dissolved in DMSO (15 mL) at 60° C. 1-(3-dimethylaminopropyl)-3-ethylcarbodiimide (259 mg, 1.45 mmol) was added and the reaction mixture allowed to stir at 60° C. for one hour. HPLC analysis (Sephadex G-10 column of 9.5×300 mm with an eluent of 0.05% NAN$_3$, 0.50 mL/min, 280 nm UV detector) of the reaction mixture showed only a single peak at 10.5 minutes retention time corresponding the mobility of the arabinogalactan-DTPA conjugate. No peak from 6α-Methylprednisolone at 19.5 minutes was observed, indicating complete attachment (by esterification) of the steroid to the arabinogalactan-DTPA conjugate. After addition of water (10 mL), the reaction mixture was ultrafiltered using an Amicon YM3 (3,000 dalton cutoff) and washed with water (3×30 mL). The filtrate contained unreacted steroid, carbodiimide, traces of DTPA and other low molecular weight materials. HPLC analysis of the filtrate confirmed the absence of free steroid. Water (10 mL) was added to the retentate and the product lyophilized. Yield of off-white powder: 0.10 g.

What is claimed is:

1. A method for the targeting of a therapeutic agent to a selected population of cells capable of receptor mediated endocytosis (RME) comprising:
   (i) forming a complex of the therapeutic agent with a polysaccharide molecule selected from the group consisting of arabinogalactan and hydrolyzed products thereof, the polysaccharide molecule being capable of interacting with an RME cell receptor; and
   (ii) allowing the complex to be internalized into the selected population of cells by receptor mediated endocytosis.

2. A method according to claim 1, wherein the therapeutic agent includes a compound containing iron.

3. A method according to claim 1, wherein the therapeutic agent includes methotrexate.

4. A method according to claim 1, wherein the therapeutic agent includes an antiviral agent.

5. A method according to claim 4, wherein the therapeutic agent includes Ara A-phosphate.

6. A method according to claim 1, wherein the therapeutic agent includes trifluorthymidine.

7. A method according to claim 1, wherein the therapeutic agent includes a hormone.

8. A method according to claim 7, wherein the hormone includes a corticosteroid.

9. A method according to claim 7, wherein the hormone includes 6α-methylprednisolone.

10. A method according to claim 1, wherein the therapeutic agent includes a nucleic acid.

11. A method according to claim 1, wherein the therapeutic agent includes an enzyme.

12. A method according to claim 1, wherein the therapeutic agent includes a vitamin.

13. A method according to claim 12, wherein the vitamin is folic acid.

\* \* \* \* \*